(12) United States Patent
Kale et al.

(10) Patent No.: US 10,531,839 B2
(45) Date of Patent: Jan. 14, 2020

(54) SYSTEM AND METHOD OF MARKING CARDIAC TIME INTERVALS FROM THE HEART VALVE SIGNALS

(71) Applicant: AventuSoft, LLC, Boca Raton, FL (US)

(72) Inventors: Kaustubh Kale, Royal Palm Beach, FL (US); Luis Gonzalo Sanchez Giraldo, Miami, FL (US); Diego Pava, Coral Springs, FL (US); Mahdi Esfahanian, Boca Raton, FL (US)

(73) Assignee: AventuSoft, LLC, Boca Raton, FL (US)

( * ) Notice: Subject to any disclaimer, the term of this patent is extended or adjusted under 35 U.S.C. 154(b) by 241 days.

(21) Appl. No.: 15/397,138

(22) Filed: Jan. 3, 2017

(65) Prior Publication Data

US 2017/0188866 A1    Jul. 6, 2017

Related U.S. Application Data

(60) Provisional application No. 62/274,766, filed on Jan. 4, 2016, provisional application No. 62/274,761, filed (Continued)

(51) Int. Cl.
*A61B 5/11* (2006.01)
*A61B 5/00* (2006.01)
(Continued)

(52) U.S. Cl.
CPC .......... *A61B 5/7282* (2013.01); *A61B 5/0006* (2013.01); *A61B 5/0008* (2013.01); *A61B 5/0022* (2013.01); *A61B 5/0044* (2013.01); *A61B 5/0205* (2013.01); *A61B 5/02028* (2013.01); *A61B 5/02438* (2013.01); (Continued)

(58) Field of Classification Search
CPC ........................... A61B 5/1102; A61B 5/0456
See application file for complete search history.

(56) References Cited

U.S. PATENT DOCUMENTS 7,096,061 B2    8/2006  Arad
7,174,203 B2    2/2007  Arand et al.
(Continued)

OTHER PUBLICATIONS

Capan; Bernstein, et al.; Measurement of Ejection Fraction by Bioimpedeance . . . , Critical Care Med.; Apr. 1987, vol. 15, Issue 4, p. 402.
(Continued)

*Primary Examiner* — George R Evanisko
(74) *Attorney, Agent, or Firm* — Pablo Meles

(57) ABSTRACT

A system for marking cardiac time intervals from heart valve signals includes a non-invasive sensor unit for capturing electrical signals and composite vibration objects, a memory containing computer instructions, and one or more processors coupled to the memory. The one or more processors causes the one or more processors to perform operations including separating a plurality of individual heart vibration events into heart valve signals from the composite vibration objects, and marking cardiac time interval from the heart valve signals by detecting individual heartbeats and processing cumulative energy within the individual heartbeat to set a threshold to set a marking point.

20 Claims, 8 Drawing Sheets

Related U.S. Application Data on Jan. 4, 2016, provisional application No. 62/274,763, filed on Jan. 4, 2016, provisional application No. 62/274,765, filed on Jan. 4, 2016, provisional application No. 62/274,770, filed on Jan. 4, 2016.

(51) Int. Cl.

| | |
|---|---|
| *A61B 5/0404* | (2006.01) |
| *A61B 5/0456* | (2006.01) |
| *A61B 5/02* | (2006.01) |
| *G16H 40/67* | (2018.01) |
| *A61B 7/04* | (2006.01) |
| *A61B 5/0205* | (2006.01) |
| *A61B 5/0468* | (2006.01) |
| *A61B 5/024* | (2006.01) |
| *A61B 5/04* | (2006.01) |
| *A61B 5/0432* | (2006.01) |
| *G06F 19/00* | (2018.01) |
| *A61B 5/046* | (2006.01) |
| *A61B 5/0472* | (2006.01) |
| *A61B 5/08* | (2006.01) |
| *G16H 50/30* | (2018.01) |
| *A61B 5/053* | (2006.01) |

(52) U.S. Cl.
CPC ........ *A61B 5/02444* (2013.01); *A61B 5/0404* (2013.01); *A61B 5/046* (2013.01); *A61B 5/04014* (2013.01); *A61B 5/04017* (2013.01); *A61B 5/0456* (2013.01); *A61B 5/0468* (2013.01); *A61B 5/0472* (2013.01); *A61B 5/04325* (2013.01); *A61B 5/1102* (2013.01); *A61B 5/6801* (2013.01); *A61B 5/6802* (2013.01); *A61B 5/6831* (2013.01); *A61B 5/6833* (2013.01); *A61B 5/725* (2013.01); *A61B 5/7214* (2013.01); *A61B 5/7225* (2013.01); *A61B 5/7275* (2013.01); *A61B 7/04* (2013.01); *G06F 19/00* (2013.01); *G16H 40/67* (2018.01); *A61B 5/024* (2013.01); *A61B 5/02055* (2013.01); *A61B 5/0536* (2013.01); *A61B 5/0816* (2013.01); *A61B 5/1107* (2013.01); *A61B 5/7203* (2013.01); *A61B 5/7246* (2013.01); *A61B 5/7257* (2013.01); *A61B 2562/0204* (2013.01); *A61B 2562/0219* (2013.01); *A61B 2562/06* (2013.01); *G16H 50/30* (2018.01)

(56) References Cited

U.S. PATENT DOCUMENTS

| | | | |
|---|---|---|---|
| 7,351,207 B2 | 4/2008 | Priemer | |
| 8,105,241 B2 | 1/2012 | Nelson et al. | |
| 8,131,354 B2 | 3/2012 | Arad | |
| 8,251,911 B2 | 8/2012 | MacQuarrie et al. | |
| 8,255,042 B2 | 8/2012 | MacQuarrie et al. | |
| 8,290,577 B2 | 10/2012 | Brooks et al. | |
| 8,475,396 B2 | 7/2013 | Jones et al. | |
| 8,614,630 B2 | 12/2013 | Narasimhan et al. | |
| 8,688,202 B2 | 4/2014 | Brockway et al. | |
| 8,694,089 B2 | 5/2014 | Arad | |
| 8,715,206 B2 | 5/2014 | Telfort et al. | |
| 8,764,653 B2 | 7/2014 | Kaminska et al. | |
| 8,790,259 B2 | 7/2014 | Katra et al. | |
| 8,823,490 B2 | 9/2014 | Libbus et al. | |
| 8,868,175 B2 | 10/2014 | Arad | |
| 8,898,369 B1 | 11/2014 | Yang | |
| 9,035,794 B2 | 5/2015 | Narasimhan et al. | |
| 9,247,004 B2 | 1/2016 | Azimi | |
| 9,307,908 B2 | 4/2016 | Chan et al. | |
| 9,370,335 B2 | 6/2016 | Al-Ali et al. | |
| 9,445,719 B2 | 9/2016 | Libbus et al. | |
| 9,462,994 B2 | 10/2016 | Rogers et al. | |
| 2004/0006279 A1 | 1/2004 | Arad | |
| 2006/0095085 A1 | 5/2006 | Marcus et al. | |
| 2007/0219059 A1 | 9/2007 | Schwartz et al. | |
| 2011/0263994 A1 | 10/2011 | Burns et al. | |
| 2012/0209131 A1 | 8/2012 | Jones et al. | |
| 2013/0109989 A1* | 5/2013 | Busse | A61B 5/1102 600/527 |
| 2013/0245487 A1 | 9/2013 | Aga | |
| 2013/0281875 A1 | 10/2013 | Narasimhan et al. | |
| 2014/0019080 A1 | 1/2014 | Chan et al. | |
| 2014/0066795 A1 | 3/2014 | Ferdosi et al. | |
| 2014/0073982 A1 | 3/2014 | Yang et al. | |
| 2014/0200474 A1 | 7/2014 | Selvaraj et al. | |
| 2014/0275932 A1 | 9/2014 | Zadig | |
| 2014/0276127 A1 | 9/2014 | Ferdosi et al. | |
| 2015/0020571 A1 | 1/2015 | Chan et al. | |
| 2015/0038856 A1 | 2/2015 | Chan et al. | |
| 2015/0045628 A1 | 2/2015 | Moghadam et al. | |
| 2015/0065894 A1 | 3/2015 | Airaksinen et al. | |
| 2015/0164410 A1 | 6/2015 | Selvaraj et al. | |
| 2015/0164411 A1 | 6/2015 | Selvaraj et al. | |

OTHER PUBLICATIONS

W. Chan M. Woldeyohannes et al.; Haemobdynamic and structural correlates . . . ; BMJ Open 2013;3:e002660.

C.L. Garrard, JR et al.; The Relationship of Alterations in Systolic . . . : Circulation. 1970; vol. 42; pp. 455-462; Amer. Heart Association.

S. Toggweiler et al: Monitoring anthracycline chemotherapy patients; 2013; Clin. Cariol.; vol. 36, Issue 4, pp. 201-206.

S. Wang et al: Rapid Bedside Identification of high-risk population; International J. of Cardiology; Jan. 24, 2013; vol. 168, pp. 1881-1886.

* cited by examiner

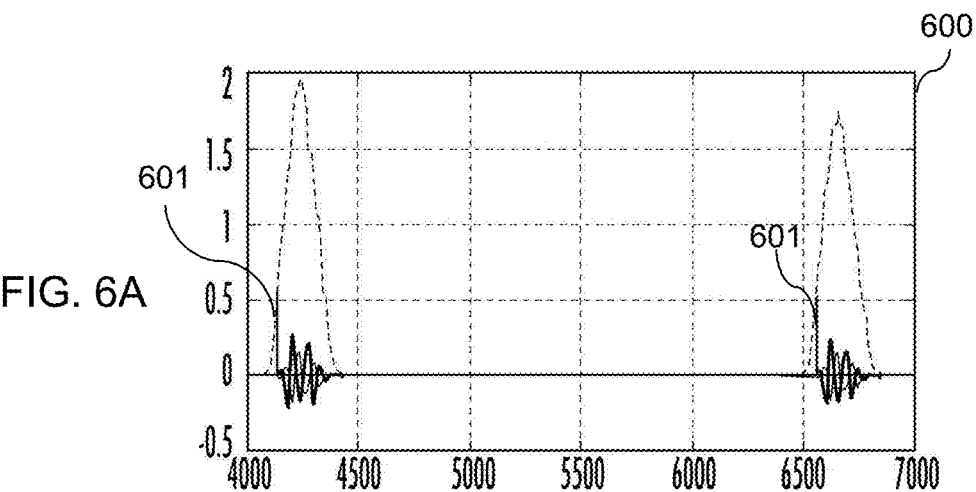

FIG. 6A

```
PARAMETERS: CUMULATIVE ENERGY THRESHOLD ∈
INPUTS: SOURCE SIGNAL Y_i
OUTPUTS: TIME OF EVENT VECTOR t
 1: COMPUTE Δ_i FROM Y_i
 2: COMPUTER THE LEADING RIGHT SINGULAR VECTORS u_1 AND u_2
 3: OBTAIN THE SCORE VECTORS s_1 AND s_2
 4: CALCULATE ENERGY ENVELOPE s AS SHOWN IN (5)
 5: FIND END POINTS OF ENVOLPE t_str AND t_end
 6: CALCULATE CUMULATIVE ENERGY BETWEEN (t_str)_i AND (t_end)_i
 7: ASSIGN TIME STAMP
          (t)_i = (t_str)_i + min ({t : (cum(s, (t_str)_i, (t_end)_i))_t > ∈})
```

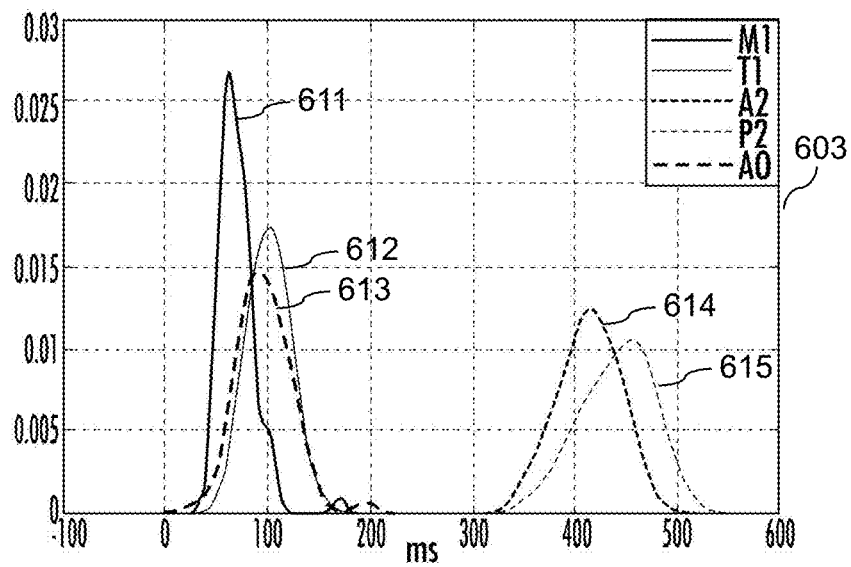

FIG. 6C

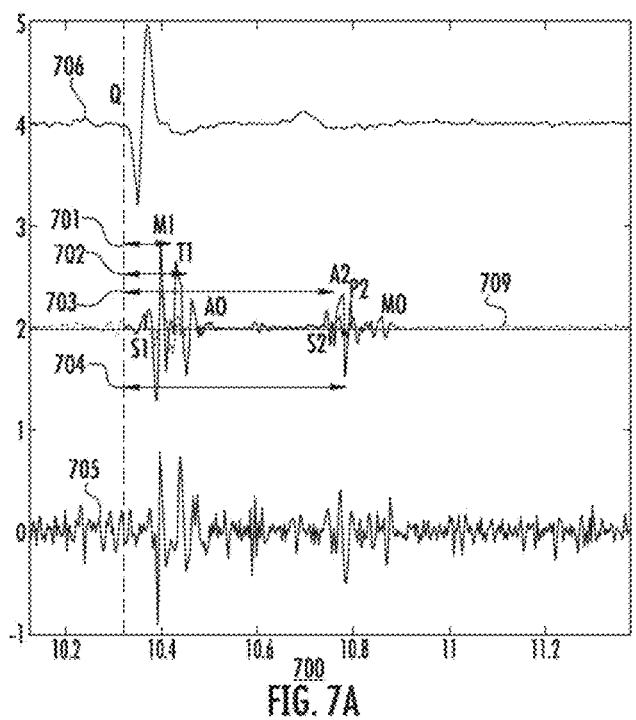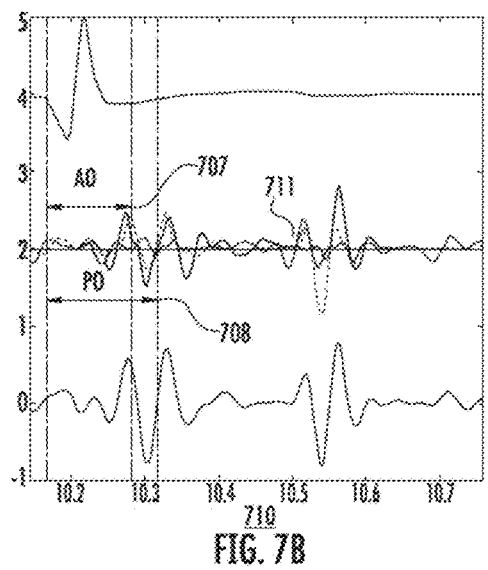
FIG. 7A
FIG. 7B

800

810

820

SYSTEM AND METHOD OF MARKING CARDIAC TIME INTERVALS FROM THE HEART VALVE SIGNALS

CROSS REFERENCE TO RELATED APPLICATIONS

This Application claims the priority benefit of Provisional Application Nos. 62/274,766, 62/274,761, 62/274,763, 62/274,765, and 62/274,770 each of which were filed on Jan. 4, 2016, the entire disclosure of each are incorporated herein by reference.

FIELD

The embodiments herein relate generally to cardiopulmonary health monitoring and more particularly to analysis software combined with transducers to capture multi-channel vibration signals along with an electrocardiogram signal for the measurement of heart functions.

BACKGROUND

Heart disease is the leading cause of death accounting for more than one-third (33.6%) of all U.S. deaths. Overall cardiac health can be significantly improved by proper triage. Low invasive and non-invasive ultrasound techniques (e.g. echocardiogram) are standard procedures, but the requirement of expensive devices and skilled operators limit their applicability. The following are the various types of heart disease that can be diagnosed and treated using the separated signal, namely, Coronary artery disease, Heart murmurs and valve abnormalities, Heart failure, Heart rhythm abnormalities (arrhythmias), Vascular disease, congenital heart disease, Cardiac resynchronization and Risk factor modification. A physician can work with patients to perform a comprehensive evaluation and design a personalized plan of care aimed at keeping them healthy.

The cardio pulmonary system which consists of the respiratory components, snoring components, and cardiac components, creates vibrations during each cardiac cycle. The vibrations are the result of the lung sounds, heart sounds, acceleration and deceleration of blood due to abrupt mechanical opening and closing of the heart valves during the cardiac cycle.

SUMMARY

The exemplary embodiments herein provide a method and system of marking cardiac time intervals from the source separated heart valve signals from the composite cardiac vibration objects. In some embodiments, data is obtained using a tri-axial accelerometer or multiple tri-axial accelerometers placed on different points of torso. The present technology pertains in general to technology for assessment of cardiac contractility in a subject from the source separated signals from recorded precordial acceleration signals. The embodiments herein can use machine learning, Principal Component Analysis (PCA), Singular Value Decomposition (SVD), k nearest neighbors, Linear LDA, Quadratic LDA, Linear SVM, or rbf SVM or others.

Examples of cardiac vibration objects are the first sound, the second sound, the third sound, the fourth sound, ejection sounds, opening sounds, murmurs, heart wall motions, coronary artery sounds, and valve sounds of the Mitral valve opening and closing, Aortic valve opening and closing, Pulmonary valve opening and closing, Tricuspid valve opening and closing. Examples of the pulmonary vibration objects are the respiratory lung sounds, breathing sounds, tracheobronchial sounds, vesicular sounds, Broncho vesicular sounds, snoring sounds. A portion of the energy produced by these vibrations lies in the infra-sound range, which falls in the inaudible and low sensitivity human hearing range. A portion of the energy produced by these vibrations falls in the audible hearing range. For example, the vibration objects from the Mitral, Tricuspid, Aortic, and Pulmonary valve openings fall in a lower range of vibrations such as 0 to 60 Hertz, whereas vibration objects from the Mitral, Tricuspid, Aortic, and Pulmonary valve closings fall in a higher range of vibrations such as 50 to 150 Hertz. Accelerometer transducers placed on the chest capture these vibrations from both these ranges.

Source separation analysis extract individual vibration objects from the composite vibration signal captured on the surface (of the torso or elsewhere). The individual vibration signals are identified to be from the mitral valve, aortic valve, tricuspid valve, and the pulmonary valve during individual heart beats. Along with separating breathing sounds, and heart wall motion. The identified valve signals are marked to indicate their start and end of the event with respect to the start of the EKG to provide the cardiac time intervals as described in the embodiments herein. These events correspond to the opening and closing of each valve. Further note that the techniques and methods herein are not limited to acoustic, electrical or vibrational data as might be used in some stethoscopes, but can also be applied to other forms of monitoring such as echo imaging or sonograms, magnetic resonance imaging (MRI), computed tomography (CT) scanning, positron emission tomography (PET) scanning, and monitoring using various forms of catheterization. The techniques and methods herein are primarily applicable to monitoring of heart valve events, but can be alternatively applied to other types of involuntary biological signaling emanating from the brain, intrauterine, pre-natal contractions, or elsewhere within both humans and other species.

DESCRIPTION OF THE DRAWINGS

FIGS. 6A, 6B, and 6C illustrate a method and a cardiac time interval measurement in accordance with one embodiment;

FIGS. 7A and 7B illustrate the marking of vibration objects or each valve into individual streams in accordance with one embodiment.

DETAILED DESCRIPTION

Figure 1A:
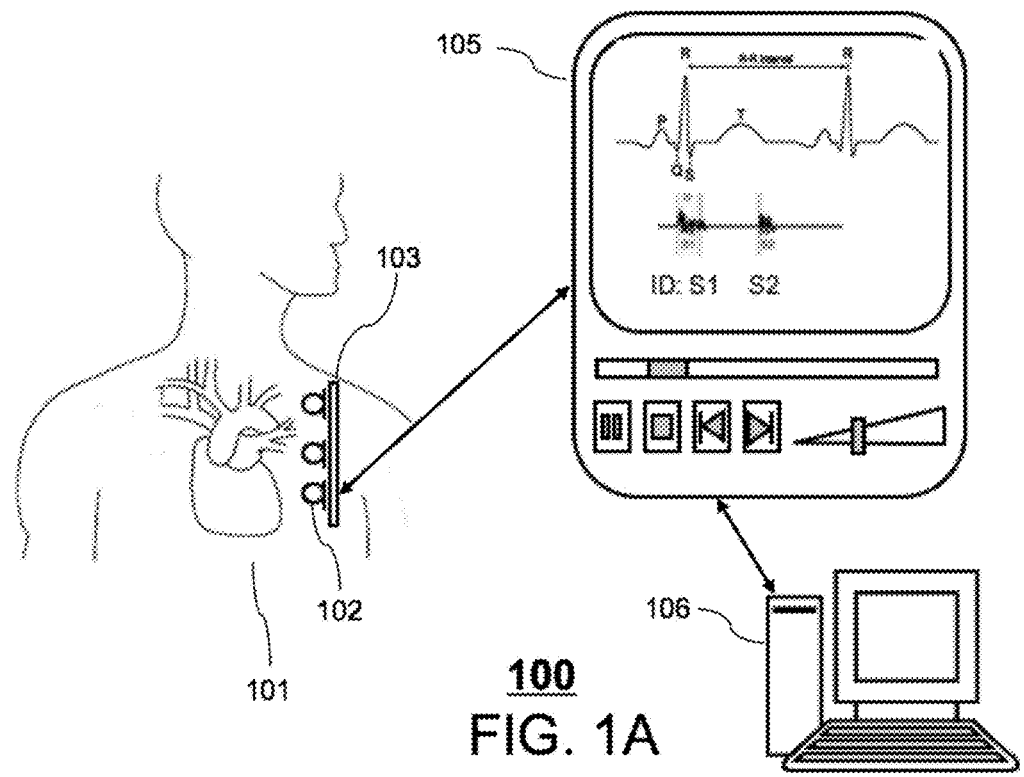
FIG. 1A illustrates a system for the extraction, identification, marking and display of the heart valve signals in accordance with one embodiment.

The exemplary embodiments may be further understood with reference to the following description and the appended drawings, wherein like elements are referred to with the same reference numerals. The exemplary embodiments describe a system and method of marking the cardiac time intervals and display of the heart valve signals. Specifically, psychoacoustics are considered in identifying the separated cardiac vibration signals captured through the transducers. The system, the psychoacoustics, and a related method will be discussed in further detail below.

The exemplary embodiments provide a novel approach for small, portable, robust, fast and configurable source separation based software with transducer hardware. The use of a vibration signal pattern and novel psychoacoustics help bypass conventional issues faced by linear time invariant systems. Clinical indices of myocardial contractility can be categorized as follows based on pressure measurements (such as dP/dtmax), volume and dimension (such as stroke volume and ejection fraction) and systolic time intervals (such as pre-ejection period, left ventricular ejection time and isovolumic contraction time). dP/dtmax is the gold standard of measurement of myocardial contractility. Some of the cardiac time intervals can include Left Ventricular Systolic Time (LVST), Left Ventricular Diastolic Time (LVDT), Pre-atrial Diastolic Filling Time (PADT), Accelerated Atrial Filling Time (AAFT), QS1 (Electromechanical activation time), QS2, Pre-Ejection Period (PEP), Right Ventricular Systolic Time (RVST), Left Atrial Systolic Time (LAST), Right Atrial Systolic Time (RAST), Right Ventricular Ejection Fraction (RVEF), Right Ventricular Diastolic Time (RVDT), Left Atrial Diastolic Time (LADT), Right Atrial Diastolic Time (RADT), Systolic Time Interval (PEP/LVST).

Figure 1B:
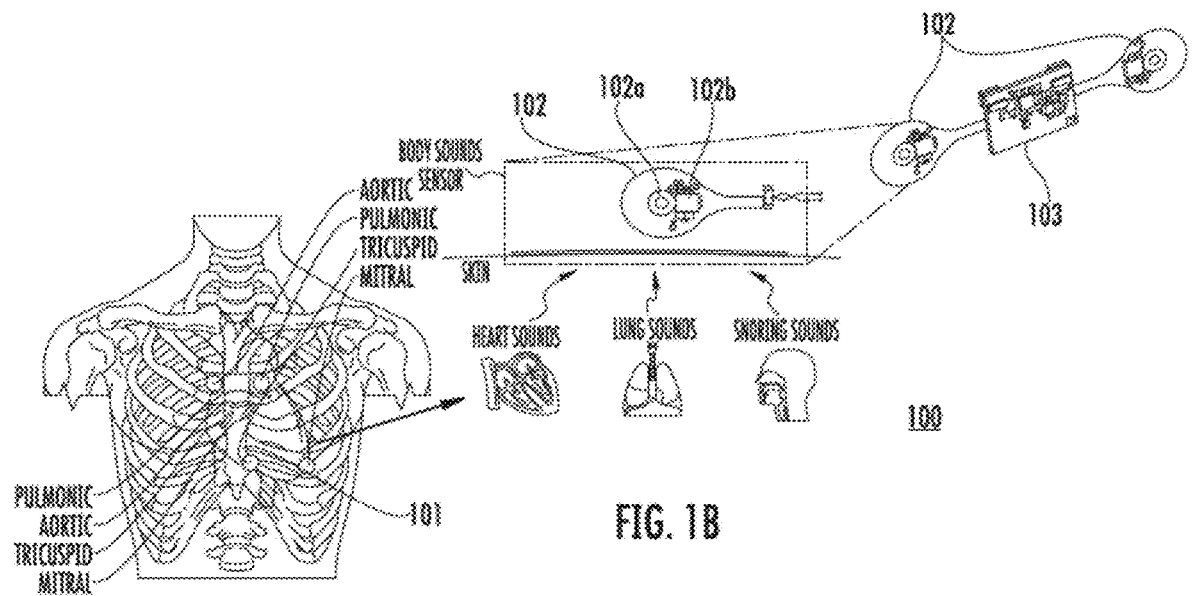
FIGS. 1B and 1C illustrate cardio pulmonary signal capture at the chest in accordance with various embodiments.
Figure 1C:
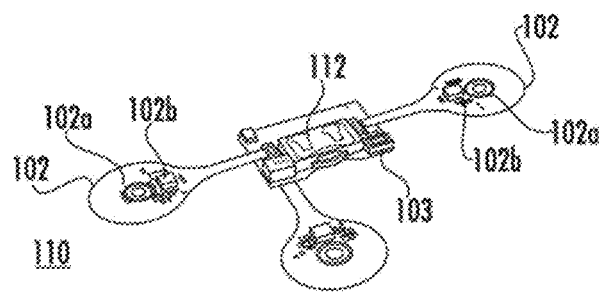

The exemplary embodiments of the system and method proposed here are shown in FIGS. 1A, 1B, and 1C. System 100 shown in FIGS. 1A and 1B is an embedded platform which can be any smart processing platform with digital signal processing capabilities, application processor, data storage, display, input modality like touch-screen or keypad, microphones, speaker, Bluetooth, and connection to the internet via WAN, Wi-Fi, Ethernet or USB. This embodies custom embedded hardware, smartphone, iPad-like and iPod-like devices. Area 101 in FIGS. 1A and 1B is the auditory scene at the chest locations. Array 102 in FIGS. 1A and 1B is the transducer array used to capture the heart signal(s). In some embodiments, the transducer array includes a pad that includes a vibration sensor such as a vibration sensor 102b and an electrode 102a for an ECG sensor. In some embodiments, the transducer array can include a single pad, two pads as shown in FIG. 1B or more than two pads as shown in FIG. 1C. In the particular embodiment of FIG. 1C, a transducer array 110 includes three pads (102) where each pad includes the vibration sensor 102b and the ECG electronic 102a. Other embodiments can include three or more pads where each pad would have at least a vibration sensor and optionally an electrode for the ECG sensor. Hardware 103 in FIGS. 1A-C is the wearable microprocessor hardware with digital signal processing capabilities, application processor, Analog to digital frontend, data storage, input modality like buttons, and wireless connection via Bluetooth, Bluetooth low energy, near field communication transceiver, Wi-Fi, Ethernet or USB.

Processor 112 shown in FIG. 1C comprises of the signal processing module on the wearable device that captures synchronized sensor data from the transducer array 102. The processor 112 is configured to save the synchronized sensor data to memory and communicate it with the system 100 for data transfer. Module 105 in FIG. 1A is the module that calculates vital sign from the input sensor stream coming from hardware 103 for the Heart rate, breathing rate, EKG signal, skin temperature, and associated vitals. The hardware 103 can optionally encrypt the raw sensor data for transmission to the cloud computing module 106. It can also communicate with a dashboard on module 105 or 106 for data exchange, login, alerts, notifications, display of processed data. Computing device 106 in FIG. 1A is the cloud module that processes the individual streams for eventual source separation. In some embodiments, the system 100 could include a connected display or other modality of display or presentation device. In some embodiments the system 100 allows a user to visually see the individual streams and information of the different cardiopulmonary signals.

The transducer array 102 can include multiple sensor transducers that capture the composite signal that includes the electrocardiogram signals, heart sounds, lung sounds and snoring sounds for example. The module 103 can be in the form of wearable hardware that synchronously collects the signals across the transducers and is responsible for the analog to digital conversion, storage and transmission to a portable unit 104. Note that the embodiments herein are not limited to processing the individual streams for source separation, identification and marking of the heart valve signals at the cloud computing module 106 only. Given sufficient processing power, the aforementioned processing can occur at the microprocessor hardware module 103, at the module 105, or at the cloud-computing module 106, or such processing can be distributed among such modules 103, 105, or 106.

Figure 2:
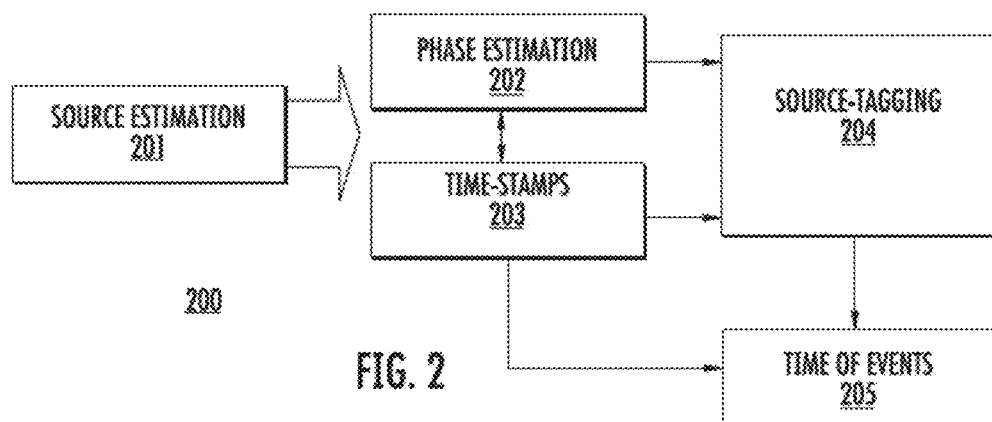
FIG. 2 is a flowchart of a method practiced by the system in accordance with one embodiment.

The exemplary embodiments of the system and method proposed here for the source identification of the cardiopulmonary signals 200 are shown in FIG. 2. Block 201 indicates the separation of sources from the composite signals. Block 202 represents the phase estimation between the separated sources at each of the sensor position. Block 203 represents calculating the time stamps of individual sources at each heartbeat with respect to the synchronized EKG signal and the other sensor or sensors. Block 204 represents the source identification module responsible for tagging each of the separated source in individual heart beats to be one of the heart valve event, namely Mitral valve closing and opening, Tricuspid valve closing and opening, Aortic valve opening and closing, and the Pulmonic valve opening and closing. Block 205 represents the time marking module to estimate the time of occurrence of the above mentioned valve events with respect to the start of the EKG signal.

Figure 3:
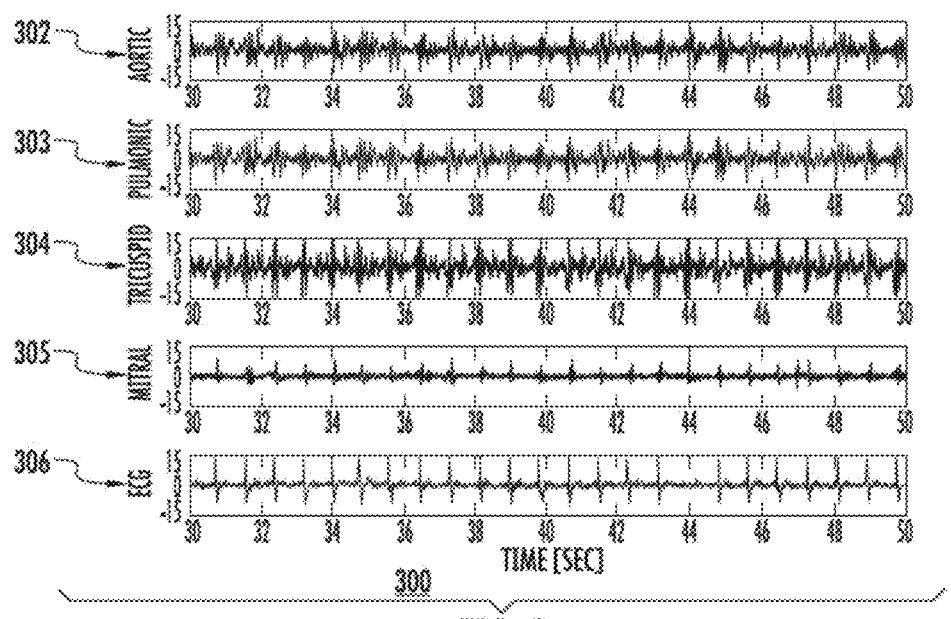
FIG. 3 illustrates multichannel signals captured from the sensor array on the chest shown in accordance with one embodiment.

The exemplary embodiments of the system and method proposed here for the source identification of the cardiopulmonary signals from the composite signal 300 are shown in FIG. 3. Area(s) 101 in FIG. 1B indicate the locations at which the composite heart signal can be captured. A vibration signal 302 as charted on the first line in FIG. 3 represents a signal captured at the aortic auscultation location. A vibration signal 303 shows the vibration signal captured at the pulmonic auscultation location. A vibration signal 304 shows the vibration signal captured at the tricuspid auscultation location. A vibration signal 305 represents a vibration signal captured at the mitral auscultation location. The last or bottom line in FIG. 3 represents an electrocardiogram signal 306 captured. In some embodiments, note that the number of sensors used (such as in the sensor array 102 of FIG. 1), are less than the number of vibration sources. For example, 3 sensors can be used to ultimately extract signals for 4 (or more) vibration sources; or 2 sensors can be used to ultimately extract signals for 3 or 4 (or more) vibration sources; or 1 sensor can be used to ultimately extract signals for 2, or 3, or 4 (or more) vibration sources.

Figure 4:
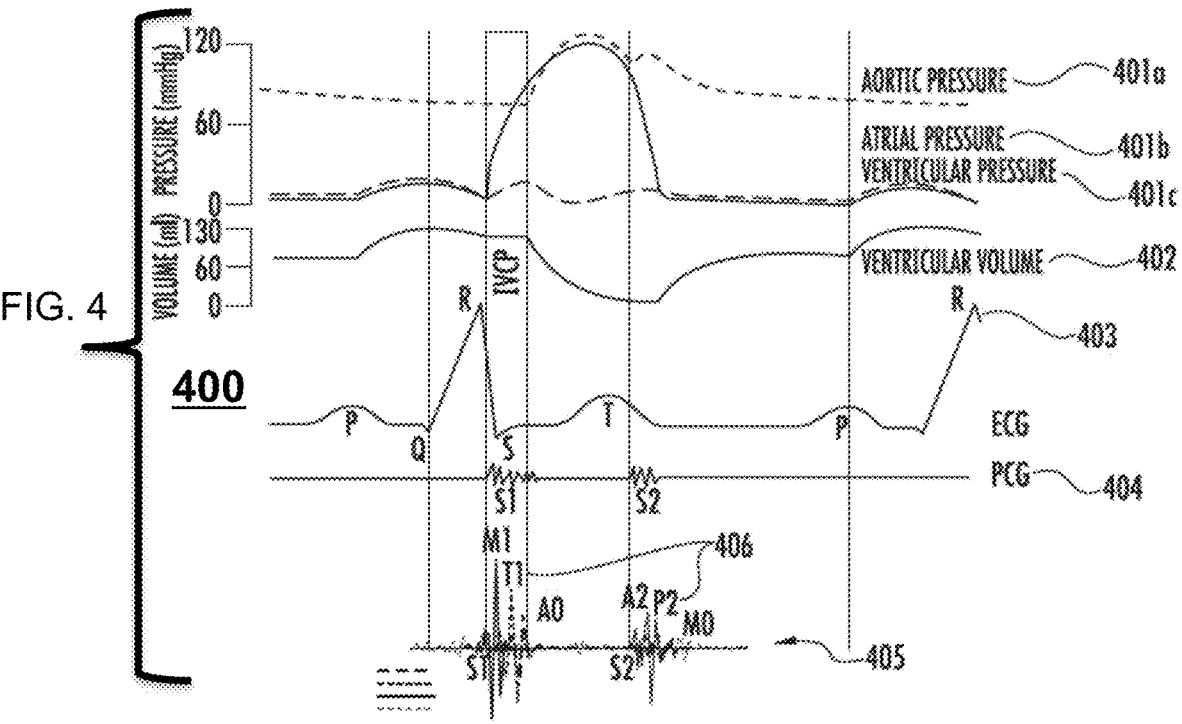
FIG. 4 illustrates a cardiac cycle in relation with Electrocardiogram, acoustic and accelerometer sensors of the system in accordance with one embodiment.

The exemplary embodiments of the system and method proposed here draw inspirations from biology with respect to the cardiac cycle in-relation with electrocardiogram and accelerometer transducer captured cardiac signal. A timeline chart 400 in FIG. 4 shows a cardiac cycle. Lines or signals 401*a*, 401*b*, and 401*c* represent or indicate the pressure changes during a cardiac cycle for aortic pressure (401*a*), atrial pressure (401*b*) and ventricular pressure (401*c*) measured in measured in millimeters of mercury (mmHg). Line or signal 402 represents or indicates the volume changes during a cardiac cycle in milliliters (ml). Line or signal 403 represents or indicates the electrical changes during a cardiac cycle captured by an electrocardiogram. Line or signal 404 represents or indicates the acoustic changes during a cardiac cycle captured by an acoustic sensor such as a phonocardiogram or PCG. S1 represents the first heart sound or the "lub" sound and the S2 represents the second heart sound or "dub" sound. Line or signal 405 represents or indicates the vibration changes during a cardiac cycle captured by an accelerometer transducer at the location of the device. Pattern 406 in FIG. 4 indicates the different valve opening and closing seen in line or signal 405 as captured by the accelerometer sensor or sensors. More specifically, a closer inspection of the pattern 406 reveals the closing of the mitral valve (M1) and tricuspid valve (T1) during the S1 or first heart sound and the closing of the aortic valve (A2) and pulmonary valve (P2).

Figure 5:
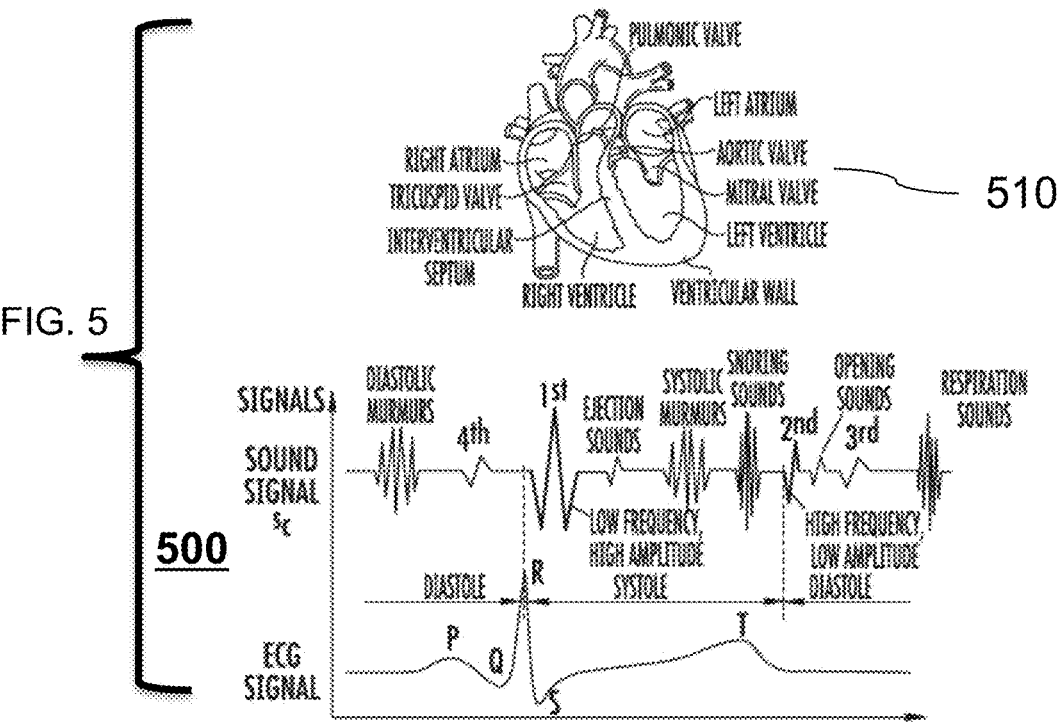
FIG. 5 illustrates a heart anatomy and schematic representation of the cardiopulmonary sounds in relation to electrocardiogram.

FIG. 5 goes on to further show a representation 510 of the human heart relevant for the generation of the sounds and corresponding graph 500 representing the sounds belonging to coronary artery, murmurs, first sound, second sound, third sound, fourth sound, ejection sounds, opening sounds, respiratory sound, breathing, and snoring during individual heart beats, with respect to the electrocardiogram signal.

The exemplary embodiments of the system and method proposed here provide a source marking algorithm for the vibrations from the cardiohemic system. In some embodiments, the system next uses PCA to determine which source is associated with which event (e.g., Mitral closing & opening, Tricuspid closing & opening, Aortic opening & closing, Pulmonic opening and closing). The following describes the architecture for automatic source tagging and timing of valvular events. One way to identify which events are relevant to a source is by manually tagging the sources against the synchronized EKG signal and taking advantage of the timings relative to a QRS wave (identification of the S1 and S2 sounds using the EKG signal as the reference has been widely researched in studies). Another approach is an automatic tagging algorithm. The tagging is composed of a classifier preceded by a feature extraction algorithm. For the timing, the system exploits the computations of one of the feature extraction algorithms to obtain an energy contour from which the time location of a given event can be inferred. Because the embodiments here build upon having the ability to capture the signal at different locations simultaneously, to the proposed system exploits the relations among channels to extract additional information about the sources. Likewise, since some source separation algorithms where channels relations are associated with location, the system can leverage on the intrinsic relations among the channels to extract relevant information that helps the system distinguish among the events. In some embodiments, the system hypothesizes that phase information between channels is relevant for distinguishing among cardiac events since valves are located at different positions within the heart. Perhaps, one of the most distinctive features of the cardiac events is their relative order of occurrence, which repeats periodically with each heartbeat. Time information extracted from the set of sources can be utilized to localize the occurrence of each source signal within the heart cycle. Therefore, the features proposed here are conceived to provide three aspects: 1) Spectral information, 2) Relations among channels, and 3) Relations among events in the form of relative times of occurrence.

The automated timing is obtained from the separated sources. The embodiments can employ the eigenfilter approach described above to extract energy envelopes that can be easily detected and further processed to extract a time point. In this case, the system uses the two leading right singular vectors of the tap-delay matrix. It has been observed that, for a single channel, the first two right singular vectors of the tap-delay matrix contain oscillatory components with $\pi/2$ phase delay. This behavior can be extended to the two-channel case by noticing that the first half of the two leading singular vectors contain an oscillatory component of similar frequency with the above mentioned $\pi/2$ phase difference for channel 1, and that the same result applies to the second half for channel 2. From the above observation, we can consider the first 2 leading right singular vectors as a quadrature pair of eigenfilters. In other words, these filters have the same magnitude in frequency with a $\pi/2$ phase difference. The sum of instantaneous energies for the quadrature pair provides an energy envelope that, for the source signals, can be processed in a simple way to obtain time stamps on the occurrence of the events associated with the source. Let u1 and u2 be the two leading right singular vectors of $\Delta i$. Let $s_1 = \Delta_i u_1$ and $s_2 = \Delta i u_2$ be the score vectors. The energy envelope s can be calculated as $(s)_i = (s_1)_i^2 + (s_2)_i^2$. From the sparsity property of the heart sounds, it is possible to detect single heart beats from the energy contour s since the source signal is mostly zeroes followed by the oscillations related to the event at each heart beat. A simple marking procedure can be obtained by first detecting individual heartbeats and then processing the cumulative energy within a heartbeat to set a threshold that defines the marking point. Process 602 shown in the box 610 of FIG. 6B describes the procedure. A resulting time stamp (black vertical lines) 601 (in chart 600 of FIG. 6A) using the energy threshold can be marked. Notice that the endpoints of the Heart valve signal have been also detected as part of the procedure in determining the time stamps 601. The chart 600 shows the resulting markings using a cumulative energy to provide a threshold. In this case 1% of cumulative energy was selected to provide the threshold value. Chart 603 shows the time intervals found for the Mitral closing (611), Tricuspid closing (612), Aortic opening (613), Aortic closing (614) and Pulmonic closing (615).

The exemplary embodiments of the system and method proposed here provide a source marking algorithm that allows from the explanation earlier for the marking of the Mitral valve closing (MC), Mitral valve opening (MO), Aortic valve opening (AO), Aortic valve closing (AC), Tricuspid valve closing (TC), Tricuspid valve opening (TO), Pulmonary valve closing (PC) and Pulmonary valve opening (PO) signals. The extracted individual valve vibration objects are aligned into a signal for each of the four valves across multiple heart beats. The chart 700 in FIG. 7A shows the source separation of heart valve opening and closing signals. Line 701 indicates the length or duration of the vibration signal for the Mitral valve closing (M1). Line 702 indicates the length or duration of the vibration signal for the Tricuspid valve closing (T1). Line 703 indicates the length or duration of the vibration signal for the Aortic valve closing (A2). Line 704 indicates length or duration of the vibration signal for the Pulmonic valve closing (P2). Signal 705 indicates the composite vibration signal captured by a particular transducer. Signal 706 indicates the EKG signal captured by the system. Referring to chart 710 of FIG. 7B, the Line 707 indicates the length or duration of the vibration of the Aortic valve opening (AO). Line 708 indicates the length or duration of the vibration of the Pulmonic valve opening (PO). Further note that the lines or signals 709 in FIG. 7A or 711 in FIG. 7B are actually several separated superimposed signals representing the vibration signals from separate sources coming from the mitral valve, tricuspid valve, aortic valve, and pulmonary valve (using less than 4 vibration sensors to extract such separated signals in some embodiments.

Figure 8A:
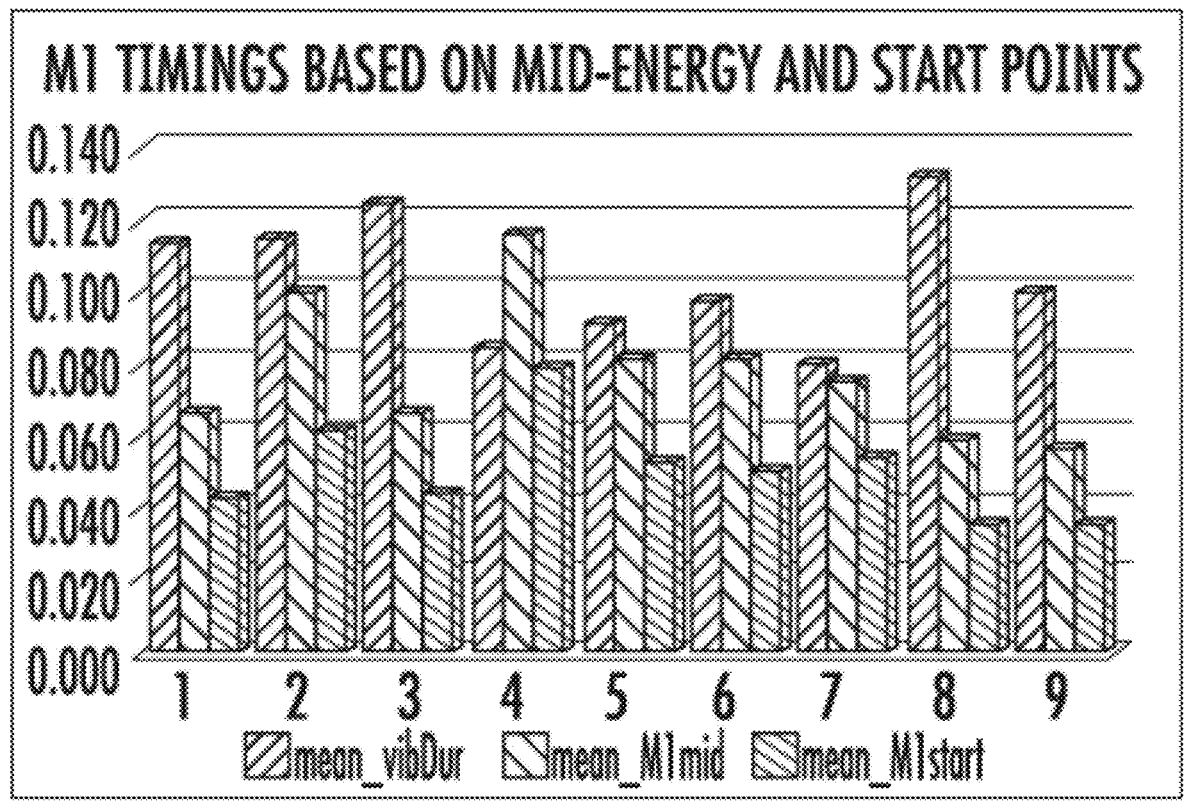
FIGS. 8A, 8B, and 8C illustrate the comparison of M1, T1, A2, and P2 timings and comparison of time calculations using different energy thresholds in accordance with one embodiment.
Figure 8B:
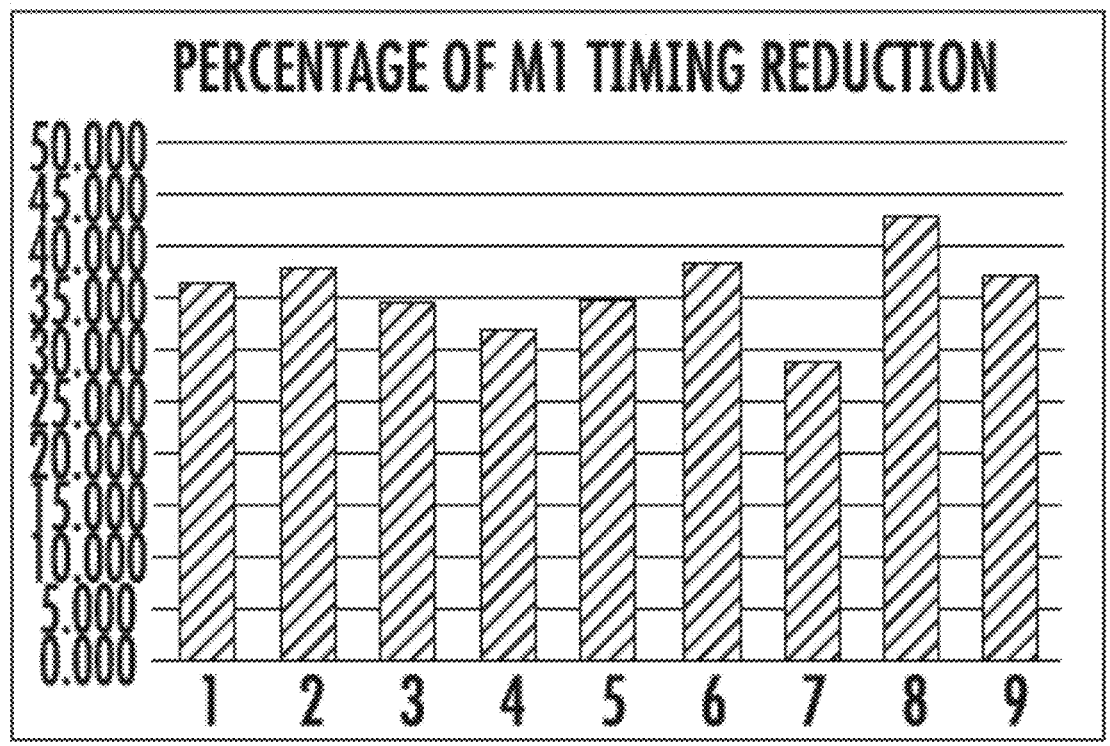
Figure 8C:
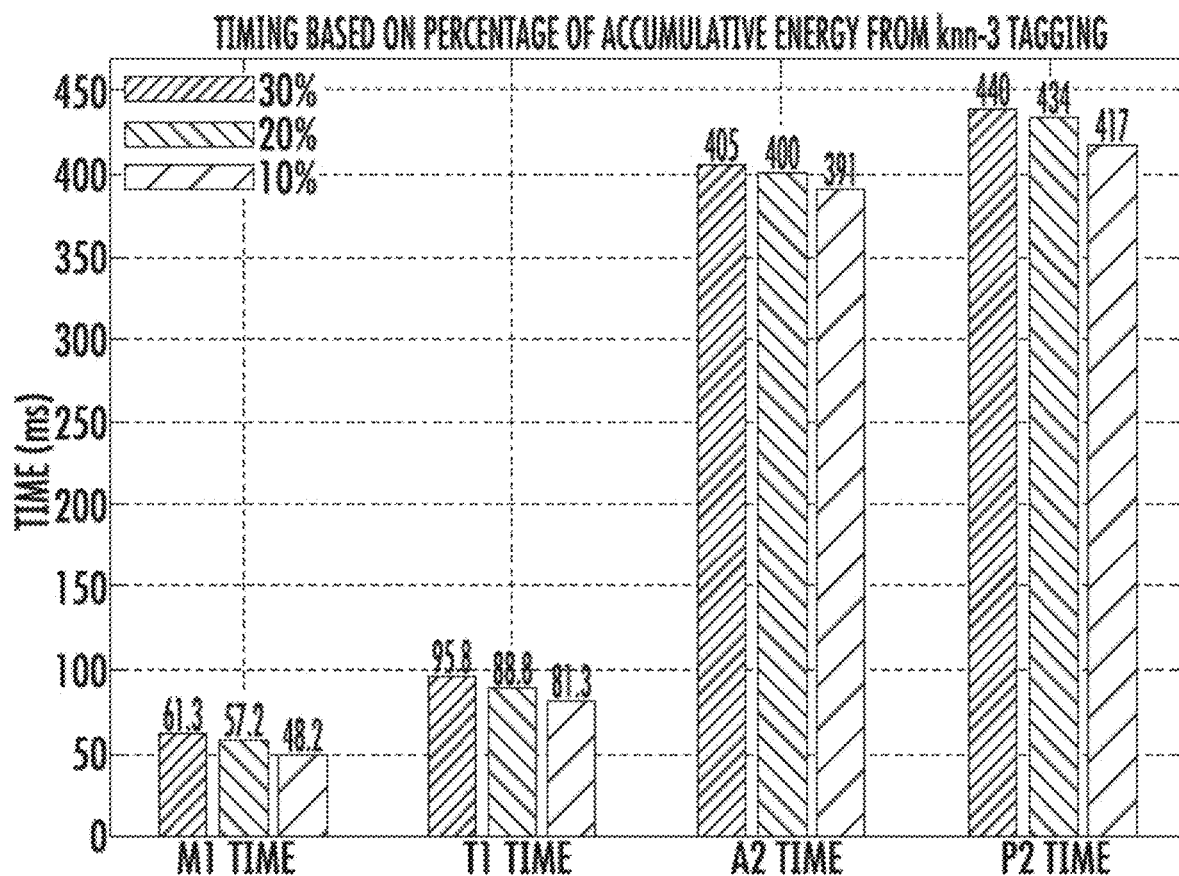

It was observed that peak of T1 timing distribution is close to that of AO. The reason is that the length of M1 and T1 Source Separation vibrations is longer than the length of AO Source Separation vibrations. So when the mid-point of accumulative energy is calculated, M1 and T1 timings are already shifted forward and don't represent the start of the vibration. Such a timing shift exists for AO but it's not as big as M1 and T1. To verify and compare, the following time information on some patients helps provide different approaches: Mean length of M1, T1 vibration, Mean start point of M1, T1 vibration, Mid-energy point is obtained from PCA algorithm. A shift back in timing of M1, T1, A2, P2 by reducing the 50% of accumulative energy to 30%, 20%, and 10%. The results are demonstrated in FIGS. 8A, 8B and 8C.

In the exemplary embodiments, a novel way of calculating the timing of the source separated individual heart vibration events from the composite vibration objects captured via multiple transducers is used to work on a single package, easy-to-use and portable device.

The exemplary embodiments develop a novel method of source timing, which in one embodiment using the Pulmonary and Aortic, and in addition possibly the Tricuspid and Mitral auscultation locations, lends the system capable of calculating the time intervals of individual valve events from the vibrations with respect to the electrocardiogram.

The exemplary embodiments develop a novel method of time interval calculation, which in one embodiment using the Pulmonary and Aortic, and in addition possibly the Tricuspid and Mitral auscultation locations, lends the system capable of marking the time of occurrence of the individual valve events with respect to the electrocardiogram. The novel method lends the system capable of measuring the cardiac time intervals.

The exemplary embodiments develop a novel method of providing time intervals of individual valve signals over time. The novel method allows for both short-term and long-term discrimination between signals. Short-term pertains to tracking individual stream when they are captured simultaneously as part of the composite signal. Long-term tracking pertains to tracking individual streams across multiple heart beats, tracking valve signals as they transition in and out during each cardiac cycle.

The exemplary embodiment of system and method described is the development on an embedded hardware system, the main elements required to capture body sounds are the sensor unit that captures the body sounds, digitization, and digital processing of the body sounds for noise reduction, filtering and amplification. Of course, more complicated embodiments using the techniques described herein can use visual sensors, endoscopy cameras, ultrasound sensors, MRI, CT, PET, EEG and other scanning methods alone or in combination such that the monitoring techniques enable improvement in terms of source separation or identification, and/or marking of events such as heart valve openings, brain spikes, contractions, or even peristaltic movements or vibrations. Although the focus of the embodiments herein are for non-invasive applications, the techniques are not limited to such non-invasive monitoring. The techniques ultimately enable diagnosticians to better identify or associate or correlate detected vibrations or signaling with specific biological events (such as heart valve openings and closings, brain spikes, fetal signals, or pre-natal contractions.)

It will be apparent to those skilled in the art that various modifications may be made in the present invention without departing from the spirit or scope of the invention. Thus, it is intended that the present invention cover the modifications and variations of this invention provided they come within the scope of the method and system described and their equivalents.

What is claimed is:

1. A system for marking cardiac time intervals from heart valve signals, comprising:
   multiple channels;
   a presentation device or a display;
   a non-invasive sensor unit for capturing electrocardiogram signals and composite vibration objects over the multiple channels;
   a memory containing computer instructions; and
   one or more processors operatively coupled to the memory and the presentation device, an execution of the computer instructions by the one or more processors causing the one or more processors to perform operations comprising:
     separating a plurality of individual heart vibration events from the composite vibration objects; and
     marking cardiac time intervals by measuring the time of occurrence of the individual heart vibration event with respect to the start of the electrocardiogram signal, measuring cumulative energy within the individual heart vibration event and processing the cumulative energy within the individual heart vibration event, and setting an energy threshold defining a marking point for the occurrence of each of the heart vibration events based on the processed energy;
   wherein the one or more processors present at least the marking point for each cardiac time interval via the display or the presentation device.

2. The system of claim 1, wherein separating the plurality of individual heart vibration events from the composite vibration objects is done by using at least one among bin-wise clustering and permutation alignment, non-negative matrix factorization, deep belief networks, or by using a classifier preceded by a feature extraction algorithm.

3. The system of claim 1, wherein the one or more processors tag the plurality of individual heart vibration events using at least one among principal component analysis, Gabor filtering, generalized cross correlation, phase transform, smoothed coherent transformation, Roth correlation, band filtering, spectral information, relations among channels, or relations among events in the form of relative times of occurrence.

4. The system of claim 1, wherein the one or more processors set the marking points by determining at least one among a mean length of an M1 vibration, a mean length of a T1 vibration, a mean start point of the M1 vibration, a mean start point of the T1 vibration, or a mid-energy point of the T1 vibration or the M1 vibration.

5. The system of claim 1, wherein the one or more processors set the marking points by shifting back in timing of an M1 vibration, a T1 vibration, an A1 vibration and a P2 vibration from 50% of the accumulative energy to one of at least 1% of the accumulative energy.

6. The system of claim 1, wherein the non-invasive sensor unit is configured to capture electrocardiogram signals and composite vibration objects at different locations simultaneously.

7. The system of claim 1, wherein the non-invasive sensor unit is configured to capture electrocardiogram signals and composite vibrations objects over the multiple channels to provide spectral information, relationships among the multiple channels, and relationships among individual heart vibration events in terms of relative times of occurrence.

8. The system of claim 1, wherein the non-invasive sensor unit comprises at least one or more sensors using a tri-axial accelerometer configured for placement on different points of a torso.

9. The system of claim 1, further comprising a sensor within the non-invasive sensor unit for capturing the electrocardiogram signals and wherein the non-invasive sensor unit comprises at least one sensor for sensing a heart valve opening.

10. The system of claim 1, wherein the one or more processors perform source separation of the composite vibration objects using a permutation alignment.

11. The system of claim 1, wherein the one or more processors perform source separation of the composite vibration objects to provide source separated signals, and then source tags the source separated signals into different heart vibration events.

12. The system for measuring cardiac time intervals of claim 1, wherein the non-invasive sensor unit comprises at least one sensor for sensing vibrations corresponding to a heart valve opening.

13. The system for measuring cardiac time intervals of claim 1, wherein one or more processors perform source separation of the composite vibration objects to provide source separated signals and wherein a number of vibration sensors in the non-invasive sensor unit which includes two or more vibration sensors is less than a number of sources for the source separated signals where the number of sources includes three or more sources.

14. The system of claim 1, wherein the processor uses at least one among Principal Component Analysis (PCA), machine learning, Singular Value Decomposition (SVD), k nearest neighbors, Linear LDA, Quadratic LDA, or Support Vector Machine (SVM), to find timing information for the individual heart vibration events and delay between the multiple channels and to determine which source is associated with which heart valve signal.

15. The system of claim 1, wherein the marking of cardiac time intervals comprises at least the marking of one or more among a Mitral valve opening (MO), Aortic valve opening (AO), Tricuspid valve opening (TO), Pulmonary valve opening (PO), a third sound, a fourth sound, murmurs, heart wall motions, a coronary artery sound, pulmonary vibration objects, a brocho vesicular sound, or cardiac time intervals within a uterus.

16. A sensor array device, comprising:
multiple channels;
a wearable device having at least one vibration sensing transducer and at least one electrode, the wearable device configured to capture an electrocardiogram signal from the at least one electrode, the electrocardiogram signal synchronized with composite vibration objects captured from at the least one vibration sensing transducer and further configured to communicate with a wireless node over the multiple channels;
wherein the at least one vibration sensing transducer is configured for capturing the composite vibration objects;
and
one or more processors operatively coupled to the wearable device and configured for:
separating a plurality of individual heart vibration events from the composite vibration objects;
marking cardiac time intervals by measuring the time of occurrence of the individual heart vibration event with respect to the start of the electrocardiogram signal, measuring cumulative energy within the individual heart vibration event, processing the cumulative energy within the individual heart vibration event, and setting an energy threshold defining a marking point for the occurrence of each of the heart vibration events based on the processed energy; and
generating signals for presenting the marked cardiac time intervals.

17. The sensor array of claim 16, wherein the marking of the cardiac time interval is one or more among a Left Ventricular Systolic Time (LVST), a Left Ventricular Diastolic Time (LVDT), a Pre-atrial Diastolic Filling Time (PADT), an Accelerated Atrial Filling Time (AAFT), a QS1 (Electromechanical activation time), a QS2, a Pre-Ejection Period (PEP), a Right Ventricular Systolic Time (RVST), a Left Atrial Systolic Time (LAST), a Right Atrial Systolic Time (RAST), a Right Ventricular Ejection Fraction (RVEF), a Right Ventricular Diastolic Time (RVDT), a Left Atrial Diastolic Time (LADT), a Right Atrial Diastolic Time (RADT), or a Systolic Time Interval (PEP/LVST.

18. The sensor array device of claim 16, wherein the at least one vibration sensing transducer is configurable for measuring a lower frequency range vibration signal and a higher frequency range vibration signal.

19. The sensor array device of claim 16, wherein the processor is operatively coupled to the at least one vibration sensing transducer, the processor further being configured for:
identifying the plurality of individual heart vibration events from the composite vibration objects;
transmitting the composite vibration signals or the plurality of individual heart vibration events to a remote device; and
marking and presenting individual valve events from the plurality of individual heart vibration events with respect to the electrocardiogram signal.

20. A method for marking cardiac time intervals from heart valve signals, comprising:
capturing electrocardiogram signals and composite vibration objects over multiple channels using a non-invasive sensor unit;

separating a plurality of individual heart vibration events from the composite vibration objects using one or more processors; and marking cardiac time intervals by measuring the time of occurrence of the individual heart vibration event with respect to the start of the electrocardiogram signal, measuring cumulative energy within the individual heart vibration event and processing the cumulative energy within the individual heart vibration event setting an energy threshold defining a marking point for the occurrence of each of the heart vibration events based on the processed energy using the one or more processors;

wherein the one or more processors present at least the marking point for each cardiac time interval to a display.

* * * * *